Jan. 21, 1964 M. L. NIES Plant Pat. 2,344
GRAPEVINE
Filed Aug. 29, 1961
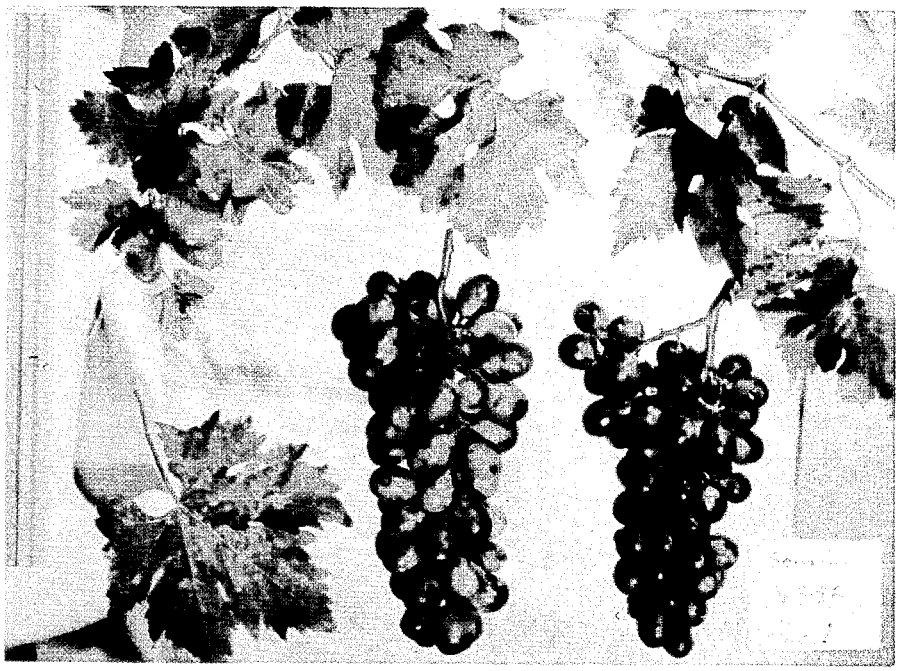
INVENTOR
MARVIN L. NIES
BY
TOWNSEND and TOWNSEND
Attorneys United States Patent Office Plant Pat. 2,344
Patented Jan. 21, 1964

2,344
GRAPEVINE

Marvin L. Nies, Rte. 1, P.O. Box 408, Lodi, Calif.

Filed Aug. 29, 1961, Ser. No. 134,788
1 Claim. (Cl. Plt.—47)

This invention relates to a new and distinct variety of grapevine obtained by crossing Queen with Cardinal. Queen is a cross between Muscat Hamburg and Thompson Seedless and Cardinal is a cross between Flame Tokay and Ribier. All of the abovementioned varieties are unpatented. Cuttings were taken at Lodi, California, in 1957 from the original seedlings employed. They were then transferred to an area a short distance from Thermal, California, in Coachella Valley. At this latter location, the first fruit was obtained in 1959 and again in 1960. Observations reported here were made on the fruit of both years.

The predominant novel characteristics of this new variety of grapevine are that it has a bright red grape under hot desert conditions and the fruits mature early. In Coachella Valley the fruit matures slightly later than Perlette but before Thompson Seedless and slightly before Cardinal.

There is no existing early maturing variety that is similar to the presently claimed variety except the variety claimed in copending plant patent application 134,790 filed August 29, 1961. The variety here described is similar to its parent Queen. It is sufficient to state that the Cardinal berries are essentially round and have a purple cast as compared with the present berries which are ellipsoidal elongated in shape, smaller in size, and bright red in color. Further, whereas Cardinal has as a general condition very straggly clusters including many shot berries, the present variety is characterized generally by well filled bunches with little straggling and virtually no shot berries.

The following is a detailed description of the new variety, with color terminology and plate reference in accordance with the Horticultural Colour Chart of the British Colour Council, except where general color terms of ordinary dictionary significance are obvious:

Vine: Moderately vigorous with no particular distinguishing aspects as to habit. General overall appearance of the vine is lacy due to the deep sinuses of the leaves.

Leaves:

*Blade.*—Petiole sinus wide with no leaves being observed in which the lobes close the sinus. Inferior sinus well marked and slightly less than ½ the distance to the petiole point of attachment. Superior sinus very well marked and approximately ⅔ the distance to the point of petiole attachment.

*Color.*—Blade: Spanish green, Plate 9060/1. Petiole: Garnet Lake, Plate 828; color extends the length of the petiole; veins at the point of attachment of the blade colored approximately 1½ cm. out toward the edge of the blade.

*Pubescence.*—Upper face is glabrous, inferior face has short hairs, upright but not prominent.

Fruit:

*Berry.*—Color (measured by natural light transmitted through exercised skin): Chrysanthemum Crimson, Plate 824/3 with growing conditions at about 90° F. (average daytime maximum temperature) as the grapes approach maturity; hotter climatic conditions produce a shift toward Plate 8/22/3 to 8/22; under certain conditions the color is very similar to Flame Tokay; during ripening, color develops from the terminal portion of the berry toward the cap stem with some greenish tinges near the point of the torus; in the latter stages of ripening the chlorophyll tends to disintegrate causing the areas not deeply colored near the torus to become yellowish; the color of the whole berry then tends toward Plate 8/22 as the underlying greenish cast disappears. Size: average; 3 cm. in length and 2.2 cm. in width. Shape: ellipsoidal elongated. Flavor: neutral; normal acidity. Skin: relatively tough. Adherence: very good, smaller bunches of ½ to ¾ lb. can be lifted. Texture of flesh: very firm but some tendency to be pulpy and flaccid.

*Bloom.*—Very similar to most table grapes; calyptras shedding completely, pollen abundant, fertile; ovary small.

*Seeds.*—Generally 2 seeds per berry with 3 in the larger berries and some of the very largest have 4. None in the smaller shot berries. Approximately 60% well developed and 30% poorly developed with fine rudiments similar to Thompson Seedless. Pronounced beak. Larger seeds 8 mm. long and 4 mm. wide. Light green becoming brown with ripening. Fairly soft.

*Brush.*—8 mm. long when pulled from berry. Light green with pinkish veins occurring from the torus for approximately 2 mm.

*Size of cluster.*—Sets well with almost no tendency to set shot berries. Fairly large bunch from 1–2 lbs. Long laterals and well defined shoulders especially on larger and older vines. Some bunches as long as 26 cms. Dense and well filled.

*Pedicel.*—Heavy; generally 12 mm. in length.

*Torus.*—Heavy; 4–5 mm. in width.

*Period of ripening.*—Early. Slightly later than Perlette but before Cardinal.

Uses: Fresh fruit is delightful eating. Principally intended as a table grape.

What is claimed is:

A new and distinct variety of grapevine, herein shown and described, characterized as to novelty by its bright red ellipsoidal elongated berry and early maturation date.

No references cited.